United States Patent [19]

Kumasaka

[11] Patent Number: 6,083,212
[45] Date of Patent: Jul. 4, 2000

[54] DISPOSABLE DIAPER

[75] Inventor: Yoshinori Kumasaka, Kagawa-ken, Japan

[73] Assignee: Uni-Charm Corporation, Kawanoe, Japan

[21] Appl. No.: 09/042,627

[22] Filed: Mar. 17, 1998

[30] Foreign Application Priority Data

Mar. 17, 1997 [JP] Japan .................................. 9-062945

[51] Int. Cl.[7] .................................................. A61F 13/15
[52] U.S. Cl. ................................ 604/385.2; 604/385.1; 604/385.2; 604/358
[58] Field of Search ........................... 604/385.1, 385.2, 604/358

[56] References Cited

U.S. PATENT DOCUMENTS

| | | | |
|---|---|---|---|
| 4,427,408 | 1/1984 | Karami et al. | |
| 5,064,421 | 11/1991 | Tracy | 604/385.1 |
| 5,370,634 | 12/1994 | Ando et al. | 604/385.1 |
| 5,746,730 | 5/1998 | Suzuki et al. | 604/385.2 |
| 5,827,259 | 10/1998 | Laux et al. | 604/385.2 |
| 5,836,930 | 11/1998 | Lantz et al. | 604/378 |

FOREIGN PATENT DOCUMENTS

| | | | |
|---|---|---|---|
| 0 627 210 | 12/1994 | European Pat. Off. | |
| 3-231660 | 2/1990 | Japan | 604/385.1 |

*Primary Examiner*—John G. Weiss
*Assistant Examiner*—Miley Craig Peppers, III
*Attorney, Agent, or Firm*—Lowe Hauptman Gopstein Gilman & Berner

[57] ABSTRACT

A disposable diaper includes a topsheet, a backsheet and an absorbent core disposed therebetween to define a front waist region, a rear waist region and a crotch region therebetween. At least one of the front and rear waist regions, for example, the front waist region has a plurality of gathers along an upper zone of this waist region appearing as an elastic member contracts. These gathers are covered with a flap comprising portions of the topsheet and the backsheet extending from an upper end of the front waist region downward beyond the elastic member. A distal end of the flap is bonded to the backsheet of the front waist region at a level lower than the elastic member.

21 Claims, 2 Drawing Sheets

DISPOSABLE DIAPER

BACKGROUND OF THE INVENTION

This invention relates to a disposable infant and adult diaper for absorption and containment of urine and other bodily exudates.

Disposable diapers are well known in which an elastic member is bonded thereto under appropriate tension to extend circumferentially in proximity of the diaper waist-opening. Such an elastic member is bonded, for example, to an inner surface of at least one of a topsheet and a backsheet of the diaper defining the waist-opening and respective inner surfaces of the topsheet and the backsheet are also bonded together so that a plurality of gathers may appear in the proximity of the waist-opening as the elastic member contracts.

With such known disposable diapers, the gather forming zone of the diaper often gives a wearer an uncomfortably rough touch and deteriorates a feeling to wear particularly when plural rubber threads having a relatively high modulus of elasticity are bonded to the diaper with a high elongation percentage so that a plurality of fine gathers may repeatedly appear along these rubber threads.

SUMMARY OF THE INVENTION

In view of the problem as described above, it is a principal object of the invention to provide a disposable diaper so improved that, even if a plurality of fine gathers appear in the proximity of a waist-opening of a diaper, wearing comfort will not be deteriorated by these gathers.

The object set forth above is achieved, according to the invention, by a disposable diaper comprising a liquid-permeable topsheet, a liquid-impermeable backsheet and a liquid-absorbent core disposed between these two sheets to define a front waist region, a rear waist region and a crotch region extending between the front and rear waist regions, wherein at least one of the front and rear waist regions is provided circumferentially along an upper waist zone in the proximity of a waist-opening of the diaper with an elastic member bonded to the associated waist region under appropriate tension so that a plurality of gathers may appear along the upper waist zone as the elastic member contracts.

The upper waist zone is provided with covering means extending circumferentially in parallel to the elastic member and fixed to the upper waist zone so as to cover the gathers.

The covering means may comprise portions of the topsheet and the backsheet folded along an upper edge of the upper waist zone outwardly or inwardly of the diaper so as to extend downward beyond the elastic member and to be bonded at their distal ends to the associated waist region.

The covering means may comprise a portion of the topsheet or the backsheet folded along the upper edge of the upper waist zone outwardly or inwardly of the diaper.

Alternatively, the covering means may comprise a flap formed by a portion of at least one of the topsheet and the backsheet folded along the upper edge of the upper waist zone outwardly or inwardly of the diaper so as to extend downward and, after bonded to the associated waist region of the diaper at a level lower than the elastic member, folded again toward the upper edge with a distal end of the flap being bonded to the associated waist region at a level adjacent the upper edge.

According to still another embodiment, the covering means may comprise a flap formed by a portion of at least one of the topsheet and the backsheet folded along the upper edge of the upper waist zone outwardly or inwardly of the diaper so as to extend downward, then bonded to the associated waist region of the diaper at a level lower than the elastic member, folded again toward the upper edge so as to extend upward beyond the upper edge and folded once more along the upper edge inwardly or outwardly of the diaper so as to extend downward with a distal end of the flap being bonded to the associated waist region at a level lower than the elastic member.

DESCRIPTION OF THE PREFERRED EMBODIMENTS

Figure 1:
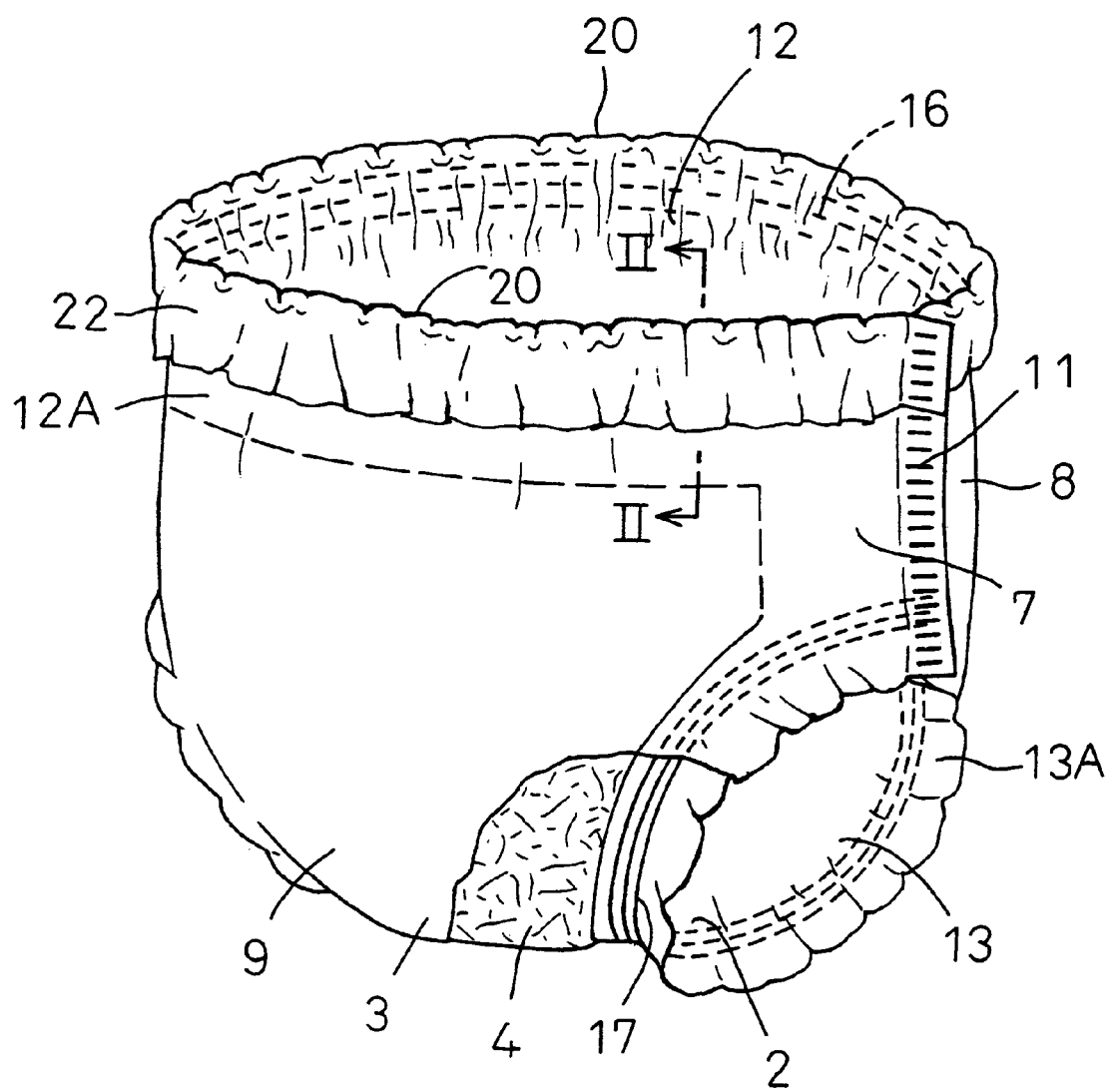
FIG. 1 is a perspective view showing an embodiment of a disposable diaper according to the invention as partially broken away.

A disposable diaper shown by FIG. 1 in a perspective view as partially broken away is of a pull-on or pants type that comprises a liquid-permeable topsheet 2, a liquid-impermeable backsheet 3 and a liquid-absorbent core 4 disposed between these two sheets.

The diaper has a front waist region 7, a rear waist region 8 and a crotch region 9 extending therebetween which are defined by the topsheet 2, backsheet 3 and the core 4. The front and rear waist regions 7, 8 are put flat together along respective transversely opposite side edges and bonded together at spots 11 intermittently arranged along these side edges so as to form a waist-opening 12 and a pair of leg-openings 13. The topsheet 2 and the backsheet 3 are placed one upon another and bonded together by means of hot melt adhesive as will be described later along their portions extending outward beyond a peripheral edge of the absorbent core 4. The waist-opening 12 and the leg-openings 13 are provided along their peripheral edges 12A, 13A with a waist surrounding elastic member 16 and leg surrounding elastic members 17, respectively. These elastic members 16, 17 are bonded under appropriate tension to an inner surface of at least one of the topsheet 2 and the backsheet 3.

Figure 2:
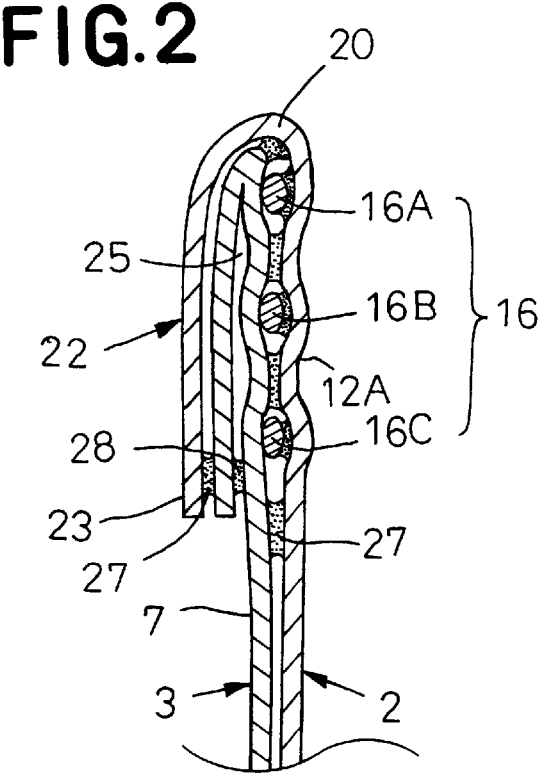
FIG. 2 is a sectional view taken along a line II—II in FIG. 1.

FIG. 2 is a sectional view taken along a line II—II in FIG. 1. The topsheet 2 and the backsheet 3 placed one upon another along an upper end 20 of the front waist region 7 are folded back along the end 20 onto the backsheet 3. The topsheet 2 and the backsheet 3 have their inner surfaces intermittently bonded to each other by means of hot melt adhesive 27. The elastic member 16 comprises three rubber threads 16A, 16B, 16C extending parallel to one another circumferentially of the diaper in this order spaced apart one from another. The respective rubber threads are bonded to at least one of the topsheet 2 and the backsheet 3 by means of adhesive 27. A flap 22 of the topsheet 2 and the backsheet 3 in the front waist region 7 folded together onto the backsheet 3 is bonded at a distal end 23 thereof at a level lower than the elastic member 16 to the backsheet 3 in the front waist region 7 by means of second hot melt adhesive 28. In this way, the flap 22 and the portion of the backsheet 3 opposed to the flap 22 form a sleeve-like configuration having a gap 25 defined therebetween. The portions of the topsheet 2 and the backsheet 3 forming flap 22 have their inner surfaces bonded together at the distal end 23. It should be understood that, between the distal end 23 and the upper end 20, the topsheet and the backsheet 3 may remain unboned together (as illustrated) or may be intermittently bonded together by means of the adhesive spots 27. The adhesive spots 27, 28 serving to bond the topsheet 2 to the backsheet 3 and to bond the folded flap 22 to the opposite backsheet 3, respectively, at the distal end 23 of the flap 22 are preferably recessed from the edge of the distal end 23 by at least 1.5 mm toward the upper end 20 of the front waist region 7. Such an arrangement is preferable to avoid any apprehension that a wearer's skin might come in contact with the adhesive spots 27, 28.

With the specific embodiment of the diaper illustrated by FIG. 1, an upper end 20 of the rear waist region 8 and an area in the proximity of the upper end 20 are also constructed as illustrated by FIG. 2.

With the diaper constructed as has been described above, an upper waist zone 12A extends circumferentially of the front and rear waist regions 7, 8 immediately below the upper end of the diaper. A plurality of relatively fine gathers each extending vertically and arranged circumferentially of the diaper appear in the upper waist zone 12A as the elastic member 16 contracts. These gathers are externally covered with the flap 22 comprising the portions of the topsheet 2 and the backsheet 3 which have been folded back together onto an outside of the diaper. The flap 22 is substantially unaffected by the contraction of the elastic member 16 and practically free from the formation of the fine gathers as formed along the peripheral edges 12A of the topsheet 2 and the backsheet 3. The flap 22 advantageously alleviates or eliminates a rough touch which otherwise would be experienced by a wearer when the wearer's hand comes in contact with the flap 22. In addition, this flap 22 can protect the wearer's skin against being accidentally scratched by the wearer's fingers holding the upper waist zone 12A. On the outer side of the front waist region 7, the distal end 23 of the flap 22 defines a stepped edge having a thickness at least corresponding to a total thickness of the topsheet 2 and the backsheet 3. When the wearer's fingers holding the upper waist zone 12A to wear the diaper, the stepped edge effectively serves as a stopper for the wearer's fingers and facilitates the diaper to be worn. With the embodiment according to which the flap 22 is folded along the upper end 20 onto an inner side of the diaper, the flap 22 prevents the gathers from being marked on the wearer's waist. It should be understood that the flap 22 may comprise only the topsheet 2 or the backsheet 3.

Figure 3:
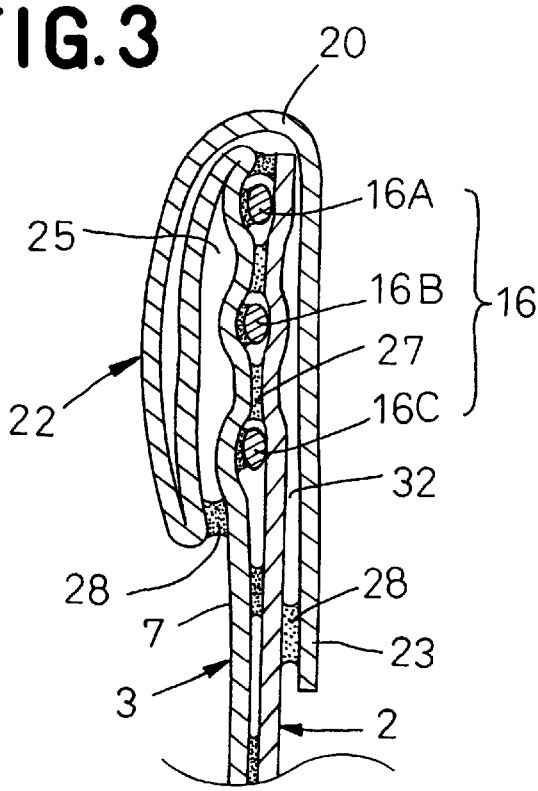
FIG. 3 is a view similar to FIG. 2 showing another embodiment of the invention.

FIG. 3 is a view similar to FIG. 2 illustrating another embodiment of the invention. According to this embodiment, the flap 22 covering the gathers comprises the backsheet 3 alone. Specifically, the backsheet 3 forming the front waist region 7 together with the topsheet 2 further extend beyond the upper end 20 of the front waist region 7 and is folded along the upper end 20 outward. The portion of the backsheet 3 thus folded outward is then bonded by means of second adhesive 28 to the backsheet 3 of the front waist region 7 at a level lower than the rubber thread 16C and folded upward. The backsheet 3 thus folded upward further extends beyond the upper end 20 of the front waist region 7 along the inside of the diaper and the distal end 23 is bonded to the topsheet 2 at a level lower than the rubber thread 16C. The flap 22 comprising the backsheet 3 alone covers the gathers from the outside as well as from the inside of the diaper leaving a gap 25 between the flap 22 and the backsheet 3 in the front waist region 7, one side, and a gap 32 between the flap 22 and the topsheet 2, on the other side. Flap 22 eliminates a rough touch of the gathers not only on the outer side but also on the inner side of the diaper. A similar effect can be obtained by the flap 22 comprising the topsheet 2 alone.

Figure 4:
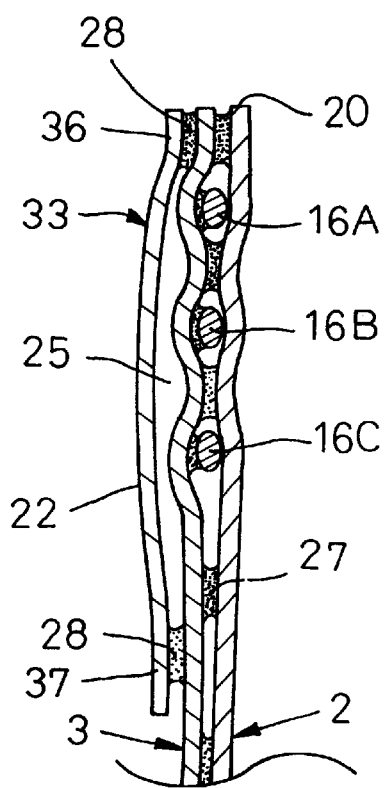
FIG. 4 is a view similar to FIG. 2 showing still another embodiment of the invention.

FIG. 4 is a view similar to FIG. 2 illustrating still another embodiment of the invention. According to this embodiment, the flap 22 covering the gathers comprises a nonwoven fabric 33. The nonwoven fabric 33 is provided in the form of belt extending circumferentially of the waist and having an upper end 36 bonded to the backsheet 3 at a level higher than the rubber thread 16A and a lower end 37 bonded to the backsheet 3 at a level lower than the rubber thread 16C, respectively by means of second adhesive 28. In this manner, there is left a gap 25 between the nonwoven fabric 33 and the backsheet 3 of the front waist region 7. The nonwoven fabric 33 may be either liquid-permeable or liquid-impermeable. A bulky nonwoven fabric made of melt blown fibers or crimped fibers is particularly preferable as the nonwoven fabric 33 in order to alleviate a rough touch peculiar to the gathers. It is also possible to employ the nonwoven fabric 33 made of material being stretchable circumferentially of the waist.

To implement the invention, a nonwoven fabric or a porous plastic film may be employed as the topsheet 2 and a plastic film or a laminate of a plastic film and a nonwoven fabric may be employed as the backsheet 3. The liquid-absorbent core 4 may be formed by fluff pulp or a mixture of fluff pulp and polymer particles of high water absorptivity. Bonding of various components may be carried out by using an suitable adhesive agent such as hot melt adhesive or heat-sealing technique.

The disposable diaper according to this invention can eliminate a rough touch of the gathers appearing at the waist level of the diaper and protect a wearer's skin against marking or scratch due to these gathers by covering these gathers with the flap comprising the topsheet and/or the backsheet or the separately prepared nonwoven fabric sheet.

What is claimed is:

1. A disposable diaper having a front waist region, a rear waist region and a crotch region extending between said front and rear waist regions, said diaper comprising:

a liquid-permeable topsheet, a liquid-impermeable backsheet and an absorbent core disposed therebetween;

at least one of said front and rear waist regions being provided circumferentially along an upper waist zone in proximity of a waist opening of said diaper with an elastic member which is secured to the associated waist region under tension so that a plurality of gathers appear along said upper waist zone as said elastic member contracts;

said upper waist zone including a cover for covering a zone of said gathers, said cover having a sheet formed without any elastic attached thereto and having a proximal edge extending circumferentially along an upper edge of said upper waist zone and a distal edge extending downward below said elastic member, said cover being secured at said proximal and distal edges to said upper waist zone.

2. A disposable diaper according to claim 1, wherein said cover comprises portions of said topsheet and said backsheet folded along said upper edge of said upper waist zone outwardly or inwardly of said diaper to extend downward beyond said elastic member.

3. A disposable diaper according to claim 1, wherein said cover comprises a portion of said topsheet or said backsheet folded along said upper edge of said upper waist zone outwardly or inwardly of said diaper.

4. A disposable diaper according to claim 1, wherein said covering means comprises a flap formed by a portion of at least one of said topsheet and said backsheet folded along said upper edge of said upper waist zone outwardly or inwardly of said diaper to extend downward and, after joined to said upper waist zone at a level lower than said elastic member, folded again toward said upper edge with a distal edge of said flap being joined to said upper waist zone at a level adjacent said upper edge of said upper waist zone.

5. A disposable diaper according to claim 1, wherein said cover comprises a flap formed by a portion of at least one of said topsheet and said backsheet folded along said upper edge of said upper waist zone toward one of outer and inner sides of said diaper to extend downward, then joined to said upper waist zone at a level lower than said elastic member, folded again toward said upper edge to extend upward beyond said upper edge and folded once more along said upper edge toward the other of said outer and inner sides of said diaper to extend downward with a distal edge of said flap being joined to said waist region at a level lower than said elastic member.

6. A disposable diaper according to claim 1, wherein said cover comprises a sheet member prepared separately of said topsheet and said backsheet.

7. A disposable diaper according to claim 6, wherein said separately prepared sheet member is stretchable circumferentially of said diaper.

8. A disposable diaper according to claim 6, wherein said separately prepared sheet is a nonwoven fabric.

9. The diaper of claim 6, wherein the cover covers only an outer surface of the diaper.

10. A disposable diaper according to claim 1, wherein said topsheet is made of a nonwoven fabric.

11. The diaper of claim 1, wherein the cover covers only an outer surface of the diaper.

12. The diaper of claim 1, wherein a lowermost portion of said cover is bonded to one of said topsheet and backsheet by means of adhesive that is recessed away from a lowermost edge of said lowermost portion.

13. The disposable diaper of claim 1, wherein portions of said cover move substantially independently relative to elevationally adjacent portions of the upper waist portion containing the gather by forming a gap between the cover and gather to eliminate bunching of the cover.

14. A disposable diaper having a front waist region, a rear waist region and a crotch region extending between said front and rear waist regions, said diaper comprising:
   a liquid-permeable topsheet, a liquid-impermeable backsheet and an absorbent core disposed therebetween;
   at least one of said front and rear waist regions being provided circumferentially along an upper waist zone in proximity of a waist opening of said diaper with an elastic member which is secured to the associated waist region under tension so that a plurality of gathers appear along said upper waist zone as said elastic member contracts;
   said upper waist zone being provided with a cover which covers a zone of said gathers and has a proximal edge extending circumferentially along an upper edge of said upper waist zone and a distal edge lying downward beyond said elastic member, said cover being joined at said proximal and distal edges with said upper waist zone and containing no elastic between said proximal and distal edges so that said cover and a portion of said upper waist zone opposed to said cover form a sleeve having a gap defined therebetween.

15. The diaper of claim 14, wherein the sleeve is hollow in the circumferential direction.

16. The diaper of claim 14, wherein a lowermost portion of said cover is bonded to one of said topsheet and backsheet by means of adhesive that is recessed away from a lowermost edge of said lowermost portion.

17. The disposable diaper of claim 14, wherein portions of said cover move substantially independently relative to elevationally adjacent portions of the upper waist portion containing the gather by forming a gap between the cover and gather to eliminate bunching of the cover.

18. A disposable diaper having a front waist region, a rear waist region and a crotch region extending between said front and rear waist regions, said diaper comprising:
   a liquid-permeable topsheet, a liquid-impermeable backsheet and an absorbent core disposed therebetween;
   at least one of said front and rear waist regions being provided circumferentially along an upper waist zone in proximity of a waist opening of said diaper with an elastic member which is secured to the associated waist region under tension so that a plurality of gathers appear along said upper waist zone as said elastic member contracts;
   said upper waist zone including a cover material extending over to cover said gathers in an area adjacent at least one of said topsheet and backsheet, said cover material being unattached to said at least one of the topsheet and backsheet in an area overlying said gathers.

19. The diaper of claim 18, wherein said cover material is connected, at a distal edge thereof, to said at least one of the topsheet and backsheet and is formed without any elastic.

20. The diaper of claim 18, wherein a lowermost portion of said cover is bonded to one of said topsheet and backsheet by means of adhesive that is recessed away from a lowermost edge of said lowermost portion.

21. The disposable diaper of claim 18, wherein portions of said cover move substantially independently relative to elevationally adjacent portions of the upper waist portion containing the gather by forming a gap between the cover and gather to eliminate bunching of the cover.

* * * * *